United States Patent [19]

Schmitz

[11] Patent Number: 5,202,455
[45] Date of Patent: Apr. 13, 1993

[54] PROCESS FOR THE LIQUID-PHASE PREPARATION OF NITRILES FROM ALIPHATIC DICARBOXYLIC ACIDS

[75] Inventor: Karl Schmitz, Gladbeck, Fed. Rep. of Germany

[73] Assignee: Huels Aktiengesellschaft, Marl, Fed. Rep. of Germany

[21] Appl. No.: 755,766

[22] Filed: Sep. 6, 1991

[30] Foreign Application Priority Data

Dec. 17, 1990 [DE] Fed. Rep. of Germany ....... 4040253

[51] Int. Cl.$^5$ .................. C07C 253/22; C07C 253/20
[52] U.S. Cl. .................... 558/313; 558/311
[58] Field of Search ................ 558/313, 311

[56] References Cited

U.S. PATENT DOCUMENTS

| 2,273,633 | 2/1942 | Fluchaire et al. | 558/313 X |
|---|---|---|---|
| 2,668,175 | 2/1954 | Reppe et al. | 558/311 |
| 2,794,043 | 5/1957 | Jansen et al. | 558/313 |
| 2,802,857 | 8/1957 | Kesslin et al. | 558/313 |
| 2,809,986 | 10/1957 | Flisik et al. | 558/313 |
| 3,297,736 | 1/1967 | Schmitt et al. | 558/313 |
| 3,297,740 | 1/1967 | Schmitt et al. | 558/313 |
| 3,299,116 | 1/1967 | Romani et al. | 558/313 X |
| 3,393,222 | 7/1968 | Schwarz et al. | 558/311 |
| 3,607,906 | 9/1971 | Hofmann et al. | 558/311 |
| 3,671,566 | 6/1972 | Decker et al. | 558/313 |
| 3,707,546 | 12/1972 | Klein | 558/313 |
| 4,599,202 | 7/1986 | Dockner et al. | 558/313 |

FOREIGN PATENT DOCUMENTS

| 857194 | 11/1952 | Fed. Rep. of Germany. | |
|---|---|---|---|
| 1046601 | 12/1958 | Fed. Rep. of Germany. | |
| 1397729 | 6/1975 | United Kingdom | 558/311 |

*Primary Examiner*—Joseph P. Brust
*Attorney, Agent, or Firm*—Oblon, Spivak, McClelland, Maier & Neustadt

[57] ABSTRACT

The present invention relates to a process for the liquid-phase preparation of nitriles from aliphatic dicarboxylic acids at temperatures of about 200° to 350° C. using ammonia in the presence of a phosphoric acid-based catalyst, wherein an adsorbent for the catalyst is added to the reaction mixture.

10 Claims, No Drawings

PROCESS FOR THE LIQUID-PHASE PREPARATION OF NITRILES FROM ALIPHATIC DICARBOXYLIC ACIDS

BACKGROUND OF THE INVENTION

1. Field of the Invention:

The invention relates to an advantageous process for the liquid-phase preparation of nitriles from aliphatic dicarboxylic acids, in which, apart from phosphoric acid or polyphosphoric acid as the catalyst, an adsorbent is additionally used.

2. Discussion of the Background

Aliphatic dinitriles have gained considerable economic importance as starting materials for the preparation of the corresponding diamines. They are easily accessible from aliphatic dicarboxylic acids by reaction with ammonia at elevated temperatures in the presence of a dehydration catalyst. The preparation of nitriles from heat-stable acids is preferably carried out in the gas phase over a fixed-bed catalyst at temperatures between 300° and 550° C. In the reaction of longer-chain acids, in which decomposition reactions take place increasingly with increasing temperature, the liquid-phase preparation of nitriles is used. In this process, the reaction is carried out between 200° C. and 350° C., at which temperature the acid is present as a melt, and ammonia is introduced into the melt in the presence of a catalyst (D. T. Mowry, "The Preparation of Nitriles", Chem. Rev. 42 (1948), 191–285). In the liquid-phase preparation of nitriles, catalysts based on phosphoric acid are preferred. According to German Patent No. 734,558, phosphoric acid, or partially or completely neutralized phosphoric esters, are used for preparing adiponitrile, which is obtained from adipic acid in a maximum yield of 86.6% of theory. The catalysts used in the process have considerable disadvantages. Phosphoric acid is converted by elimination of water to polyphosphoric acid, which is deposited in the reactor. The polyphosphoric acid impairs heat transfer from the external source to the reaction mixture, and furthermore, causes corrosion. The phosphoric esters also mentioned in German Patent No. 734,558 result in the same problems, since they are hydrolysed under the conditions of nitrile preparation to form phosphoric acid, which in turn, forms polyphosphoric acid.

According to German Patent No. 857,194, a process for the preparation of dinitriles from aliphatic $\alpha,\Omega$-dicarboxylic acids in the presence of phosphoric acid or salts thereof is described. In the presence of metaphosphoric acid, sebacic acid is converted to sebaconitrile in a yield of 82.1% of theory. The catalysts phosphoric acid, metaphosphoric acid or salts thereof used in this process also lead to the formation of polyphosphoric acid, resulting in the above-mentioned difficulties with regard to deposits forming on the walls of the reactor.

U.S. Pat. No. 3,297,740, which is incorporated herein by reference, provides a further example of the many nitrile preparation processes from dicarboxylic acids in the presence of phosphoric acid. Crude trimethyladipic acid is reacted with ammonia in a stirred reactor in the presence of phosphoric acid or phosphoric acid salts at temperatures between 240° and 290° C. to give trimethyladiponitrile, while simultaneously, the reaction side-products are removed by distillation. The top side-products formed are ammonia-containing water and more volatile byproducts such as, in particular, trimethylcyclopentanone. Trimethyladiponitrile is discharged via a side outlet.

Crude trimethyladiponitrile also contains trimethyladipimide. During the subsequent washing with ammonia, it is converted into the corresponding diamide, which is passed to the reactor, and converted quantitatively into trimethyladiponitrile. Before vacuum distillation of trimethyladiponitrile, the imides of the shorter-chain acids originating from the crude trimethyladipic acid have to be removed by washing with sodium hydroxide solution. In this nitrile preparation process too, deposits of polyphosphoric acid are formed, which cause shutdowns and/or breakdowns in the reactor, and subsequent loss of production, as a result of the above-mentioned deposits of polyphosphoric acid on the walls of the reactors.

Surprisingly, it has now been found that deposits of polyphosphoric acid on the reactor walls formed in the liquid-phase preparation of nitriles from dicarboxylic acids in the presence of phosphoric acid, polyphosphoric acid and metaphosphoric acid can be prevented by adding an adsorbent to the reaction mixture.

SUMMARY OF THE INVENTION

Accordingly, one object of the present invention is to develop a process by which dicarboxylic acids can be converted with ammonia to nitriles in the liquid phase in the presence of a catalyst system which does not lead to deposits and corrosion on the walls of the reactor.

A further object of the present invention is to develop a process by which dicarboxylic acids can be converted to nitriles in the liquid phase with ammonia in the presence of a catalyst system which does not lead to extensive formation of free polyphosphoric acid.

A further object of the present invention is to develop a process by which dicarboxylic acids can be converted with ammonia to nitriles in the liquid phase in the presence of a catalyst system which does not lead to shutdowns and/or breakdowns in the reactor, and subsequent loss of production.

A further object of the present invention is to develop a process for the production of nitriles from dicarboxylic acids and ammonia by use of a catalyst system which can be easily recovered, regenerated and/or reactivated.

These and other objects which will become apparent during the following detailed discussion of the present invention, have been realized by a process for the liquid-phase preparation of nitriles from aliphatic dicarboxylic acids at temperatures of from 200° C. to 350° C. using ammonia in the presence of a phosphoric acid-based catalyst, wherein an adsorbent for the phosphoric acid-based catalyst is added to the reaction mixture, the phosphoric acid-based catalyst being, for example, phosphoric acid, polyphosphoric acid, a salt thereof, an unhydrolyzed or partially hydrolyzed ester thereof, or any mixture thereof.

DETAILED DESCRIPTION OF THE PREFERRED EMBODIMENTS

In the process of the present invention, the phosphoric acid or polyphosphoric acid catalyst is now no longer deposited on the reactor surface, but on the adsorbent, without losing its catalytic activity. After the nitrile preparation has been carried out, the catalyst system comprising an adsorbent and phosphoric acid, polyphosphoric acid and/or salts and/or esters thereof can be easily separated, recovered and used again.

However, it is also possible to work up the reaction mixture by vacuum distillation without separating and/or recovering the catalyst, and to use the distillation residue remaining after distillation as the catalyst material for the next batch. In order to avoid undue increases in the amount of distillation residue, part of it should be discharged, and the catalyst system should be replenished accordingly.

During nitrile preparation, a certain coking of the catalyst system takes place, which increases all the more, the more often the catalyst is recycled into the nitrile preparation process. Coking is defined herein as the deposition of carbonaceous material on the particles of the catalyst system. The result of coking is that the catalytic activity initially increases, but then greatly decreases upon exceeding a certain degree of coking. The decrease in catalytic activity becomes noticeable by observing the corresponding reduced rate of formation of water. After addition of phosphoric acid or other suitable catalyst, the original calalytic activity is regained.

In addition to catalytic phosphoric acid, metaphosphoric acid and/or polyphosphoric acid, other suitable catalysts include salts and esters of these acids, to be used in combination with the adsorbents, according to the present invention. An example of suitable salts of phosphoric acid, metaphosphoric acid and/or polyphosphoric acid include lithium, sodium, potassium, and ammonium salts, etc. Particularly preferred salts are ammonium salts. Esters of phosphoric acid, metaphosphoric acid, and/or polyphosphoric acid suitable for use in the present invention may be unhydrolyzed, partially hydrolyzed, or completely hydrolyzed, and further, the ester groups may be present singly or as a multiple, and more than one ester group may be present. Suitable ester groups include those disclosed in German Patent No. 734,558, and include aliphatic esters, such as methyl, ethyl, propyl, isopropyl, butyl, isobutyl, pentyl, and hexyl; cycloaliphatic esters, such as cyclopenyl and cyclohexyl; aryl esters, such as phenyl, o-tolyl, m-tolyl, p-tolyl, and naphthyl; aralkyl esters, such as benzyl; etc. The esters may also form a ring from an alkylene diol, such as ethylene glycol, 1,2-propanediol or 1,3-propanediol, and a phosphorus atom and two oxygen atoms of a phosphate salt, phosphoric acid, metaphosphoric acid or polyphosphoric acid, by elimination of water.

Suitable adsorbents for use in the present invention are kieselguhr, diatomaceous earth, celite, Tonsil bleaching earth, frankonite, silica, alumina, clays, and molecular sieves. These adsorbents are preferably in powder form. Preferred adsorbents are filtering aids based on kieselguhr, diatomaceous earth, Celite, Tonsil bleaching earth, and frankonite, and the most preferred adsorbents are kieselguhr and Tonsil bleaching earth. In general, any amount of adsorbent sufficient to prevent catalyst deposits may be used, but preferably, 50 to 200% by weight of adsorbent relative to the weight of the catalyst (e.g., phosphoric acid) is used, and most preferably, 75 to 150% by weight of adsorbent relative to the weight of the catalyst.

The aliphatic dicarboxylic acids can contain from 4 to 18 carbon atoms, and can be straight-chain or branched. Cycloaliphatic dicarboxylic acids are also suitable, and may be substituted with one or more aliphatic groups, such as lower alkyl groups. Preferable aliphatic dicarboxylic acids contain from 4 to 14 carbon atoms, and most preferably, from 4 to 10 carbon atoms. Suitable examples of aliphatic dicarboxylic acids include succinic acid, glutaric acid, adipic acid, pimelic acid, suberic acid, azelaic acid, trimethyl adipic acid, and sebacic acid, cyclopentane dicarboxylic acid and cyclohexane dicarboxylic acid. Particularly preferred aliphatic dicarboxylic acid starting materials are trimethyladipic acid and sebacic acid.

Advantageously, the catalyst system according to the present invention may be introduced into the reactor by any suitable method.

For example, the adsorbent may be impregnated with catalyst (e.g., phosphoric acid), then added to the reactor either before or during the heating phase of the reaction. Alternatively, the adsorbent and the catalyst (e.g., phosphoric acid) may be simultaneously or separately added to the already melted dicarboxylic acid, or a suspension comprising the adsorbent and an aqueous solution of catalyst (e.g., phosphoric acid) may be added to the already melted dicarboxylic acid.

The process according to the present invention is conducted at a temperature of from about 200° C. to 350° C., preferably from about 240° C. to about 320° C., and most preferably, from about 260° C. to about 300° C.

Other features of the present invention will become apparent in the course of the following description of exemplary embodiments which are given as illustration of the present invention and are not intended to be limiting thereof.

EXAMPLE 1

3,000 kg of sebacic acid are poured into a 4.7 m$^3$ stirred reactor of a nitrile preparation plant. The reactor temperature is set to 300° C. while simultaneously, ammonia gas is introduced into the reactor. During the heating phase, a catalyst system suspension prepared from 15 kg of kieselguhr filtering aid, 15 kg of phosphoric acid and 75 kg of water is metered in over a period of 1 to 2 hours. During the reaction which lasts from 30 to 35 hours, from 15 to 30 m$^3$/h of ammonia circulation gas and fresh ammonia gas are passed into the reactor. The water formed during the reaction is discharged together with the excess ammonia gas. After nitrile preparation is complete, the product is distilled off in vacuo, yielding sebaconitrile in 96.0% of the theoretical yield. The purity of the sebaconitrile product as determined by gas chromatography is 99.6%.

No polyphosphoric acid deposits could be found in the reactor. The distillation residue remaining from the vacuum distillation is used as the catalyst for subsequent reactions. After six additional reactions using the residue from the previous reaction as the catalyst system, 1.7 kg of phosphoric acid is added to the residue to regain the original catalyst activity.

EXAMPLE 2

The reaction of sebacic acid was carried out in accordance with the experimental conditions described in Example 1. Instead of the catalyst suspension, 15 kg of phosphoric acid was used as a 75% strength by weight aqueous solution. The values of yield and quality of the product were the same as those of Example 1, but polyphosphoric acid deposits were observed on the reactor walls.

EXAMPLE 3

800 g of crude trimethyladipic acid (formed in 88.5% purity during the nitric acid oxidation of trimethylcyclohexanol) are heated in a glass apparatus to 200° C. Subsequently, 4 g of kieselguhr filtering aid, then 4 g of 85% strength by weight aqueous phosphoric acid solution are added to the melt with vigorous stirring. The temperature is increased to 260° C. over the course of about 30 minutes while simultaneously passing in 50 l/h of ammonia gas. The metering-in of ammonia is then increased to 200 l/h, and the reaction temperature is kept at 260° C. for 7 hours. Ammonia water and organic byproducts (in particular, trimethylcyclopentanone) escape during the reaction at the column head, and the ammonia water is separated from the organic byproducts in the separator. Crude trimethyladiponitrile is then distilled off in vacuo. The distillation residue formed is subsequently used without further addition of phosphoric acid as the catalyst material for the following reaction. The reaction was repeated three times (four reactions in total), and the results are listed in Table 1.

EXAMPLE 4

The nitrile preparation from crude trimethyladipic acid in the presence of 4 g of 85% strength by weight aqueous phosphoric acid solution was carried out according to Example 3. In the catalyst recycling experiments (Experiments 6-8), the distillation residue from the previous reaction served as the catalyst for the subsequent experiment. The experimental results are listed in Table 2.

dicarboxylic acid and ammonia at a temperature of from 200° C. to 350° C. in the presence of a catalyst selected from the group consisting of phosphoric acid, metaphosphoric acid, polyphosphoric acid, salts of these acids, esters of these acids and mixtures thereof, said catalyst being adsorbed by an adsorbent selected from the group consisting of kieselguhr, diatomaceous earth, calite, Tonsil bleaching earth and frankonite, to produce a second liquid mixture containing said nitrile.

2. The process of claim 1, wherein said adsorbent is selected from the group consisting of kieselguhr and Tonsil bleaching earth.

3. The process of claim 1, wherein said dicarboxylic acid is a straight-chain or branched $C_{4-10}$ alphatic dicarboxylic acid.

4. The process of claim 1, wherein said dicarboxylic acid is sebacic acid.

5. The process of claim 1, wherein said dicarboxylic acid is trimethyladipic acid.

6. The process of claim 1, wherein said heating is conducted at a temperature from about 240° C. to about 320° C.

7. The process of claim 1, wherein said heating is conducted at a temperature from about 260° C. to about 300° C.

8. The process of claim 1, wherein said catalyst is phosphoric acid.

9. The process of claim 1, wherein said catalyst is

TABLE 1

| Experiment No. | Amount of Starting material (g) | Catalyst System | Separator Organic phase (g) | Separator $NH_3$—water (g) | Amount of Crude product (g) | Polyphosphoric acid deposit? | Vacuum distillation Amount of Distillate (g) | Composition by GC trimethyladiponitrile (%) | Composition by GC trimethyladipimide (%) | Distillation residue (g) |
|---|---|---|---|---|---|---|---|---|---|---|
| 1 | 800 | 4 g kieselguhr filtering aid + 4 g 85% strength by weight $H_3PO_4$ solution | 42.8 | 353 | 578 | none | 507 | 84.6 | 11.2 | 56 |
| 2 | 800 | dist. residue experiment 1 | 51.5 | 378 | 616 | none | 532 | 84.0 | 11.6 | 79 |
| 3 | 800 | dist. residue experiment 2 | 52.8 | 375 | 633 | none | 526 | 84.4 | 11.3 | 101 |
| 4 | 800 | dist. residue experiment 3 | 56.9 | 388 | 651 | none | 525 | 84.7 | 11.0 | 121 |

TABLE 2

| Experiment No. | Amount of Starting material (g) | Catalyst System | Separator Organic phase (g) | Separator $NH_3$—water (g) | Amount of Crude product (g) | Polyphosphoric acid deposit? | Vacuum distillation Amount of Distillate (g) | Composition by GC trimethyladiponitrile (%) | Composition by GC trimethyladipimide (%) | Distillation residue (g) |
|---|---|---|---|---|---|---|---|---|---|---|
| 5 | 800 | 4 g 85% strength by weight $H_3PO_4$ solution | 39.6 | 372 | 567 | deposit | 490 | 85.7 | 10.0 | 71 |
| 6 | 800 | dist. residue experiment 5 | 46.0 | 377 | 638 | deposit | 536 | 85.6 | 10.5 | 97 |
| 7 | 800 | dist. residue experiment 6 | 47.5 | 372 | 658 | deposit | 521 | 86.1 | 9.8 | 131 |
| 8 | 800 | dist. residue experiment 7 | 49.3 | 348 | 684 | deposit | 519 | 86.4 | 9.5 | 161 |

What is claimed as new and desired to be secured by Letters Patent of the United States is:

1. A process for the melt liquid phase preparation of a $C_{14-18}$ aliphatic or a $C_{5-6}$ cycloaliphatic nitrile, comprising:
heating a first liquid mixture of a straight-chain or branched $C_{4-18}$ aliphatic or a $C_{5-6}$ cycloaliphatic adsorbed onto said adsorbent prior to being in the presence of said first liquid mixture.

10. The process of claim 1, wherein said catalyst is mixed with said adsorbent and water prior to being in the presence of said first liquid mixture.

* * * * *